US012239649B2

(12) United States Patent
Kuhn et al.

(10) Patent No.: US 12,239,649 B2
(45) Date of Patent: Mar. 4, 2025

(54) DIETARY FIBER FOR TREATING PATIENTS SUFFERING FROM METHYLMALONIC ACIDEMIA AND PROPIONIC ACIDEMIA

(71) Applicant: N.V. Nutricia, Zoetermeer (NL)

(72) Inventors: Mirjam Kuhn, Utrecht (NL); Maryam Rakhshandehroo, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 1008 days.

(21) Appl. No.: 17/281,598

(22) PCT Filed: Oct. 1, 2019

(86) PCT No.: PCT/NL2019/050657
§ 371 (c)(1),
(2) Date: Mar. 31, 2021

(87) PCT Pub. No.: WO2020/071909
PCT Pub. Date: Apr. 9, 2020

(65) Prior Publication Data
US 2022/0040211 A1    Feb. 10, 2022

(30) Foreign Application Priority Data
Oct. 1, 2018  (NL) .................................... 2021737

(51) Int. Cl.
| | |
|---|---|
| *A61K 31/702* | (2006.01) |
| *A23L 33/00* | (2016.01) |
| *A23L 33/12* | (2016.01) |
| *A23L 33/125* | (2016.01) |
| *A23L 33/135* | (2016.01) |
| *A23L 33/155* | (2016.01) |
| *A23L 33/16* | (2016.01) |
| *A23L 33/175* | (2016.01) |
| *A23L 33/18* | (2016.01) |
| *A23L 33/22* | (2016.01) |
| *A23L 33/24* | (2016.01) |
| *A61K 31/202* | (2006.01) |
| *A61K 31/59* | (2006.01) |
| *A61K 31/715* | (2006.01) |
| *A61K 31/717* | (2006.01) |
| *A61K 31/718* | (2006.01) |
| *A61K 31/733* | (2006.01) |
| *A61K 31/736* | (2006.01) |
| *A61K 33/06* | (2006.01) |
| *A61K 35/745* | (2015.01) |
| *A61K 35/747* | (2015.01) |
| *A61P 7/08* | (2006.01) |

(52) U.S. Cl.
CPC .......... *A61K 31/702* (2013.01); *A23L 33/12* (2016.08); *A23L 33/125* (2016.08); *A23L 33/135* (2016.08); *A23L 33/155* (2016.08); *A23L 33/16* (2016.08); *A23L 33/175* (2016.08); *A23L 33/18* (2016.08); *A23L 33/22* (2016.08); *A23L 33/24* (2016.08); *A23L 33/40* (2016.08); *A61K 31/202* (2013.01); *A61K 31/59* (2013.01); *A61K 31/715* (2013.01); *A61K 31/717* (2013.01); *A61K 31/718* (2013.01); *A61K 31/733* (2013.01); *A61K 31/736* (2013.01); *A61K 33/06* (2013.01); *A61K 35/745* (2013.01); *A61K 35/747* (2013.01); *A61P 7/08* (2018.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2006/0286258 | A1* | 12/2006 | Petschow ................ | A23L 33/40 426/590 |
| 2009/0196921 | A1* | 8/2009 | Ebel ........................ | A61P 31/12 424/463 |
| 2014/0037603 | A1* | 2/2014 | Bolster ................ | A61K 36/064 424/769 |

FOREIGN PATENT DOCUMENTS

| | | | |
|---|---|---|---|
| WO | 2005110121 A1 | 11/2005 | |
| WO | WO-2007069900 A1 * | 6/2007 | ............. A23L 1/296 |

OTHER PUBLICATIONS

Tims, S., Marsaux, C., Pinto, A., Daly, A., Karall, D., Kuhn, M., . . . & Scholl-Bürgi, S. (2022). Altered gut microbiome diversity and function in patients with propionic acidemia. Molecular Genetics and Metabolism, 137(3), 308-322. (Year: 2022).*
Nutricia: "A food for special medical purposes; to be used under strict medical supervision", May 1, 2016.
Knol Jan et al: "Colon microflora in infants fed formula with galacto- and fructo-oligosaccharides: More like breast-fed infants", Journal of Pediatric Gastroenterology and Nutrition, Lippincott Williams Wilkins, Inc, US, vol. 40, No. 1, Jan. 1, 2005, pp. 36-42.
Matthias R Baumgartner et al: "Proposed guidelines for the diagnosis and management of methylmalonic and propionic acidemia", Orphanet Journal of Rare Diseases, Biomed Central Ltd, LO, vol. 9, No. 1, Sep. 2, 2014, p. 130.
Alberto Burlina et al: "The potential role of gut microbiota and its modulators in the management of propionic and methylmalonic acidemia", Expert Opinion on Orphan Drugs, vol. 6, No. 11, Oct. 23, 2018, pp. 683-692.
Yatsunenko et al: "Human gut microbiome viewed across age and geography", Nature, 486(7402), 222-227, Dec. 14, 2012.
Rodriguez et al: "The composition of the gut microbiota throughout life, with an emphasis on early life", Microbial Ecology in Health & Disease 2015. 26:26050.

* cited by examiner

*Primary Examiner* — Dale R Miller
(74) *Attorney, Agent, or Firm* — N.V. Nederlandsch Octrooibureau

(57) ABSTRACT

The present invention concerns a composition comprising dietary fiber for use in the dietary management of methylmalonic acidemia (MMA) and/or propionic acidemia (PA), and/or for use in treating and/or reducing MMA and/or PA, and/or treating, reducing and/or preventing symptoms associated therewith.

14 Claims, No Drawings

DIETARY FIBER FOR TREATING PATIENTS SUFFERING FROM METHYLMALONIC ACIDEMIA AND PROPIONIC ACIDEMIA

FIELD OF THE INVENTION

The present invention is related to the field of dietary management of methylmalonic acidemia (MMA) and propionic acidemia (PA), and for treating symptoms associated therewith.

BACKGROUND

Organic Acidurias (OA) patients suffer from a rare inborn error of metabolism. The largest conditions within OA are methylmalonic acidemia (MMA) and propionic acidemia (PA). Both disorders share common biochemical and clinical features resulting in the accumulation of propionyl-CoA and/or methylmalonic acid (MMA) and other metabolites, due to the deficiency of propionyl-CoA carboxylase or methylmalonyl-CoA mutase respectively. The initial symptoms of PA and MMA include poor feeding, vomiting, loss of appetite, weak muscle tone (hypotonia), and lack of energy (lethargy). These symptoms sometimes progress to more serious medical problems, including heart abnormalities (cardiomyopathy), pancreatitis, seizures, coma, and possibly death.

Propionic acid is a precursor of propionyl-CoA. Propionic acid production in humans originates from amino acid metabolism, odd-chain fatty acid metabolism, and anaerobic bacterial fermentation of dietary fibers in the gut. Next to acetate and butyrate, propionic acid is one of the main short chain fatty acids (SCFA) produced in the gut by the microbiota. A large proportion of the gut commensals from healthy adult humans carry genes for at least one of the three known propionic acid producing metabolic pathways. Even though the factors determining which pathways are active in any given human gut are unknown, activity of differential pathways will likely have consequences for the functioning of the gut microbiota. In other words, any change in the production of any of the main SCFAs, such as propionic acid, may have an effect on the substrates used by microbiota and metabolites produced by microbiota as a collective entity. The different propionic acid production (or synthesis) pathways will have different consequences on the overall SCFA production potentials (not just of propionic acid itself). It is estimated that at least 25% of the total propionic acid in MMA and PA patients originates from the gut bacteria, although this could be an underestimation as the microbiota of MMA and PA patients are currently barely characterized.

Fiber is a component of the normal diet and is widely recognized as being an important part of healthy nutrition. There are many different types of fibers which are often classified as soluble or insoluble, and can be further classified as fermentable, non- or poorly-fermentable. Fiber has been shown to have many beneficial effects on gut health including improving stool consistency, normalizing gut transit time, generating production of short chain fatty acids, and restoring a balanced gut microbiota composition. Not all types of fibers have the same qualitative or quantitative effects. The full range of health benefits of fibers can best be obtained by consumption of a variety of fiber sources. Fermentable fibers are important for generation of short chain fatty acids and restoration of a balanced microbiota. Less well fermented fibers enhance stool bulk, consistency and viscosity, and possibly contribute to reduced bacterial translocation.

Although fermentable fibers are considered beneficial as they increase the level of short chain fatty acids in the large intestine, for MMA and PA patients such increase may be unfavorable as the level of propionic acid may increase accordingly.

Prior art nutritional products intended for MMA and PA patients that are currently used often contain dietary fibers that are not optimized for use in the treatment of MMA and PA patients, since the fibers present still produce high amounts of propionic acid when fermented by intestinal microbiota. MMA/PA Anamix® Next and MMA/PA Anamix® junior comprise a digestive fiber mix to promote digestive health; the fiber mix comprises oligofructose, inulin, Gum arabic, cellulose, soy polysaccharides and resistant starch. The product comprise an amino acid composition that is methionine-, threonine- and valine-free and low in isoleucine. Both MMA/PA Anamix products are marketed for MMA/PA patients.

Knol et al. (J. Pediatr. Gastroenteral Nutr., vol 40(1), January 2005) demonstrate an infant formula comprising GOS/FOS in a 9:1 ratio to lower the ratio of propionic acid to short chain fatty acids in the feces of infants aged 7 to 8 weeks. The publication is silent on the total amount of SCFA produced. In general results for dietary fiber digestion cannot be extrapolated from infants to older aged subjects. Older aged subjects have a completely different microbiome compared to infants (Edwards and Parrett; Brit. J. Nutr. 2002, 88:Suppl. 1, S11-S18). This difference is generally attributed to the natural development of the intestinal tract, the changing nutritional pattern and in some cases events like diseases and the use of antibiotics. Also hormonal changes during adolescence may further affect the microbiome. It is believed the largest changes in the microbiome occur between an age of 0 and 3.

Venkatamaran et al (Microbiome (2016), 4:33) demonstrate no significant effect of resistant starch (type 2) on propionic acid in the stool of young adults.

It is an object of the invention to improve the known fiber compositions for MMA and PA patients, in order to optimize the general health effect of fibers through fermentation products such as lactate and butyrate, and at the same time limit the production of propionic acid when fermented by gut microbiota.

SUMMARY OF THE INVENTION

The inventors found that certain fibers and fiber mixes were capable of modulating the propionic acid production, which plays an important role in the clinical features of MMA and PA patients, and consequently also to improve gastrointestinal tract complications in these patients. The inventors found the propionic acid production can be reduced, even whilst increasing the total amount of short chained fatty acids. MMA and PA patients can therefore profit from the benefits of dietary fiber mixture of the present invention, whilst at the same time lowering the level of propionic acid and therefore improving their condition. The inventors further surprisingly demonstrated these benefits also occur in an adult population.

The examples show that galactooligosaccharides (GOS) or fiber mixes comprising GOS resulted in a lower than expected production of propionic acid by the microbiome. Also the total amount of SCFA increases for these fibers. Moreover, the inventors surprisingly found that when combining GOS with resistant starch the level of propionic acid could be further lowered, whereas prior art report resistant starch to have no effect on propionic acid formation.

LIST OF PREFERRED EMBODIMENTS

1. Composition comprising galactooligosaccharides for use in:
   treating and/or reducing methylmalonic acidemia (MMA) and/or propionic acidemia (PA), and/or treating, reducing and/or preventing symptoms associated therewith;
   dietary management of MMA and/or PA; and/or
   reducing gut flora induced production of propionic acid, in a human subject having an age of at least 3 years.
2. The composition for use according to embodiment 1, wherein the subject has an age of at least 12 years, preferably at least 18 years.
3. The composition for use according to any one of the preceding embodiments, wherein the composition further comprises resistant starch.
4. The composition for use according to any one of the preceding embodiments, wherein the composition further comprises Gum arabic, soy polysaccharides and at least one of oligofructose and inulin.
5. Composition comprising galactooligosaccharides, resistant starch, Gum arabic, soy polysaccharides and at least one of oligofructose and inulin for use in:
   treating and/or reducing methylmalonic acidemia (MMA) and/or propionic acidemia (PA), and/or treating, reducing and/or preventing symptoms associated therewith;
   dietary management of MMA and/or PA; and/or
   reducing gut flora induced production of propionic acid,
   in a patient suffering from MMA or PA.
6. The composition for use according to any one of embodiments 1-5, wherein the composition comprises at least 10 wt. %, preferably at least 20 wt. %, most preferably at least 30 wt. % resistant starch, based on the total dietary fiber weight.
7. The composition for use according to any one of embodiments 1-6, wherein the composition comprises at least 20 wt. %, preferably at least 30 wt. %, most preferably at least 50 wt. %, of the combination of resistant starch and galactooligosaccharides, based on the total dietary fiber weight.
8. The composition for use according to any of embodiments 1-7, wherein the composition further comprises lactic acid producing bacteria, preferably selected from the group consisting of Bifidobacteria and Lactobacilli.
9. The composition for use according to any of embodiments 1-8, wherein the composition further comprises guar gum.
10. The composition for use according to any of embodiments 1-9, wherein the composition comprises less than 5 wt. % cellulose, based the total dietary fiber weight, preferably the composition comprises no cellulose.
11. The composition for use according to any of embodiments 1-10, wherein the composition is in the form of:
    (i) a nutritional supplement, wherein the supplement preferably further comprises amino acids; or
    (ii) a complete nutritional composition, wherein the nutritional composition further comprises a protein fraction, preferably in the form of amino acids, digestible carbohydrates, vitamins and minerals.
12. The composition for use according to any of embodiments 1-11, wherein the composition further comprises a protein fraction consisting essentially of free amino acids and dipeptides, preferably wherein the protein fraction is substantially devoid of valine, isoleucine, methionine and threonine.
13. The composition for use according to any of embodiments 1-12, wherein the composition comprises DHA.
14. The composition for use according to any of embodiments 1-13, wherein the composition comprises vitamin D and/or calcium, preferably vitamin D.
16. Composition comprising galactooligosaccharides, resistant starch, Gum arabic, soy polysaccharides and at least one of oligofructose and inulin
17. Composition according to embodiment 16, wherein the amount of GOS is at least 5 wt %, and resistant starch is at least 10 wt. % of the dietary fiber in the composition, preferably at least 20 wt. %, most preferably at least 30 wt. %.
18. The composition according to embodiment 16 or 17, wherein the composition comprises less than 5 wt. % cellulose, based on total dietary fiber weight, preferably wherein the composition comprises no cellulose.

DETAILED DESCRIPTION OF THE INVENTION

The invention relates to a composition comprising dietary fiber, which is suitable for the dietary management of patients suffering from methylmalonic acidemia (MMA) and/or propionic acidemia (PA), as well as for treating and/or reducing methylmalonic acidemia (MMA) or propionic acidemia (PA) and/or treating, reducing and/or preventing symptoms associated therewith, as well as for reducing gut flora induced production of propionic acid, while maintaining/increasing the production of other short-chain fatty acids. The composition to be used in this respect is referred to as the composition according to the invention and is defined in detail below.

Composition

The composition according to the invention contains at least one dietary fiber and may contain further components as defined here below. In a preferred embodiment, the composition further comprises protein source consisting of a specially designed blend of free amino acids or dipeptides. This amino acid composition is a specifically selected blend of amino acids that supports growth in MMA/PA patients, and at the same time supports the effect of the selected dietary fibers in decreasing the production of propionic acid.

The composition according to the invention may also be referred to as nutritional composition. The composition may take the form of a supplement providing the dietary fiber, which can be administered to the patient in addition to the regular diet. In case the composition according to the invention is in the form of a supplement, it comprises the dietary fiber and preferably the blend of amino acids. The supplement may also be referred to as dietary supplement or nutritional supplement, and may take any form as known in the art, including tablets, capsules, (reconstitutable) powders, liquids, etc. The composition may also take the form of a complete nutritional composition, which can be administered to the patient instead of one or more meals. In case the composition according to the invention is in the form of a complete nutritional composition, it comprises dietary fiber, proteinaceous material, digestible carbohydrates, vitamins and minerals. The complete nutritional composition preferably takes the form of a liquid or a powder intended for reconstitution with a liquid. In one embodiment, the composition is a supplement. In one embodiment, the composition is a complete nutritional composition. In one embodiment, the composition is in the form of a liquid. The composition according to the invention is intended for patients suffering from MMA and/or PA, and since these patients are used to special diets to cope with their disorder, administration of the composition according to the invention is readily implemented in their daily feeding pattern.

The composition is further defined below. Herein, the term "about" signifies a margin of +/−10%.

Subject

When referred to a patient or subject, it concerns human patients or subjects.

In the context of the present invention, an infant is a subject between 0 and 1 year, a toddler a subject between 1 and 3 years, a child a subject between 3 and 12 years, a teenager a subject between 12 and 18 years, an adult a subject older than 18 years. Preferably the patient is older than 1 year, more preferably 3 years, even more preferably 12 years, even more preferably 14 years most preferably 18 years. Preferably the patient is an infant, toddler, child, teenager or adult, By the end of the first year of life, infants possess an individually distinct microbial profile, converging toward the characteristic microbiota of an adult, such that by 2-5 years of age, the microbiota fully resembles that of an adult in terms of composition and diversity. Therefore, the first 3 years of life represent the most critical period for dietary interventions to improve growth and development. This is the period when the intestinal microbiota, a vital asset for health and neurodevelopment is established and its alteration during this period has the potential to profoundly affect host health and development. Reference is made to Rodriguez et al. "*The composition of the gut microbiota throughout life, with an emphasis on early life*" Microb. Ecol. Health Dis. (2015); 26. The findings are particularly relevant for a child, teenager or adult; even more preferably the patient is a teenager or adult, most preferably the patient is an adult.

Dietary Fiber

The composition according to the invention comprises dietary fiber, which term also includes mixtures of dietary fibers. In one embodiment of the invention the dietary fiber comprises galactooligosaccharide. In another embodiment of the invention the dietary fiber comprises a mixture of galactooligosaccharide and resistant starch. In another embodiment the dietary fiber is a mixture of galactooligosaccharide, resistant starch and additional fibers. The inventors have surprisingly found that the dietary fiber or mixture of dietary fibers according to the invention reduces the amount of propionic acid formed during anaerobic fermentation as it occurs in the intestine.

In the context of the present invention, "fiber" and "dietary fiber" are used interchangeably. According to the present invention the term dietary fiber means the edible part of plants or analogous carbohydrates that are resistant to digestion and absorption in the human small intestine with complete, partial or no fermentation in the large intestine. This includes polysaccharides, oligosaccharides, lignin and associated plant substances. Preferably the dietary fiber used for the composition according to the invention is selected from the group of fermentable fibers and poorly or non-fermentable fibers. Preferably, the fibers of the mixture of dietary fibers used for the composition according to the invention are selected from both fermentable and poorly or non-fermentable fibers, more preferably a mixture of both types is used. Without being bound by theory, the inventors believe that constipation and problematic bowel movements in methylmalonic acidemia (MMA) and propionic acidemia (PA) patients are improved by the use of these poorly or non-fermentable dietary fiber. In one embodiment, the poorly or non-fermentable dietary fiber or fibers are selected from the group consisting of hemicellulose, lignin, alpha cellulose and resistant starch and mixtures thereof. In one embodiment, the fermentable dietary fiber or fibers are selected from the group consisting of oligofructose, inulin, wheat bran, gum arabic, soy polysaccharides, oat fiber, galactooligosaccharides, locus bean gum, guar gum, pectin, hydrolyzed pectin and mixtures thereof. In a preferred embodiment, the dietary fiber or fibers are selected from the group consisting of oligofructose, inulin, resistant starch, cellulose, methylcellulose preferably hydroxypropyl methylcellulose, wheat bran, gum arabic, soy polysaccharides, oat fiber, galactooligosaccharides, locus bean gum, guar gum, pectin, hydrolyzed pectin and mixtures thereof. The terms 'gum arabic' and 'arabic gum' are used interchangeably.

In one embodiment, one fiber is used, which is galactooligosaccharides. Alternatively, mixtures of distinct dietary fibers are used, such as mixtures of at least 2, at least 3, at least 4, at least 5, at least 6 or even at least 7 distinct dietary fibers are used, preferably selected from the above list of preferred dietary fibers. Preferably the mixture of fibers comprises at least galactooligosaccharides. Although the amount of distinct dietary fibers used in the context of the present invention is not particularly limited, for practical reasons at most 10, at most 9 or even at most 8 distinct dietary fibers may be used. Preferred fiber (mixtures) are as follows:

(i) The fiber is galactooligosaccharides.
(ii) The fiber mixture comprises two fibers, of which one is galactooligosaccharides.
(iii) The fiber mixture comprises two fibers, of which one is galactooligosaccharides and one is resistant starch.
(iv) The fiber mixture comprises at least three, preferably at least four, at least five or at least six fibers from which one is galactooligosaccharides and one resistant starch.
(v) Fiber mixture (ii), further comprising oligofructose and/or inulin, Gum arabic and soy polysaccharides.
(vi) Fiber mixture (iv), further comprising oligofructose and/or inulin, Gum arabic and soy polysaccharides.
(vii) Fiber mixture (ii), (iii), (iv), (v) or (vi), further comprising guar gum and/or partly hydrolyzed guar gum.
(viii) The fiber mixture comprising at least two, at least three, at least four, at least five, at least six or all seven fibers selected from the group consisting of oligofructose, inulin, resistant starch, Gum arabic, locus bean gum, galactooligosaccharides and soy polysaccharides.
(ix) The fiber mixture (ii), (iv), (v), (vi), (vii) or (viii), not comprising cellulose.
(x) The fiber mixture comprising at least two, at least three, at least four, at least five, at least six, at least seven or all eight fibers selected from the group consisting of oligofructose, inulin, resistant starch, cellulose, Gum arabic, locus bean gum, galactooligosaccharides and soy polysaccharides.

An especially preferred dietary fiber used in the composition according to the invention is GOS. GOS helps to achieve a balance between the different SCFAs produced along the length of the colon and helps to improve stool bulking properties whilst lowering the formation of propionic acid. Preferably GOS is combined with resistant starch. This combination combines the benefits of a non-fermentable dietary fiber and a fermentable dietary fiber.

Preferably, GOS or the mix of GOS and resistant starch is supplemented with other dietary fibers, preferably with a combination of Gum arabic, soy polysaccharides and oligofructose and/or inulin. This fiber mixture closely reflects the range and type of fiber habitually consumed in the normal diet and further lower the formation of propionic acid compared to GOS or the mix of GOS and resistant starch. In a preferred embodiment, the amount of resistant starch is at least 10 wt. % of the dietary fiber in the composition, more preferably at least 20 wt. %, most preferably at least 30%. In a preferred embodiment, when both GOS as resistant starch are present in a fiber mix comprising more than 2 fibers, the sum of the amount of resistant starch and galactooligosaccharides is at least 20 wt. %, preferably at least 30 wt. %, most preferably at least 50 wt. % of the dietary fiber in the composition.

Preferably GOS, the mix of GOS and resistant starch, or these fibers supplemented with a combination of Gum arabic, soy polysaccharides and oligofructose and/or inulin are supplemented with guar gum and/or partly hydrolyzed guar gum. Guar gum and/or partly hydrolyzed guar gum are fermentable fibers and may further act as a flavor masking agent and therefore may support masking any of—flavors such as bitterness of the fibers and/or the amino acids that may be comprised in the composition.

Preferably, the composition according to the invention comprises 0.4-50 g dietary fibers per 100 kcal, more preferably 0.6-30 g per 100 kcal, most preferably 1-20 g per 100 kcal, based on the total energy content of the composition (including the fibers). In case the composition according to the invention is a complete nutritional composition, the dietary fiber content is preferably 0.4-9 g dietary fibers per 100 kcal, even more preferably 0.6-7 g per 100 kcal and most preferably 0.8-3 g per 100 kcal of the composition. In case the composition according to the invention is a supplement, the dietary fiber content is preferably 2-50 g dietary fibers per 100 kcal, even more preferably between 4-30 g per 100 kcal and most preferably 5-20 g per 100 kcal of the composition. The composition according to the invention preferably comprises between 1.5 and 5 g, more preferably between 2 and 4 g, and most preferably between 2.5 and 3.5 g dietary fibers per 10 g protein. Preferably, the composition according to the invention provides between 2 and 40 g, preferably between 10 and 30 g dietary fibers in a daily dose. The actual dose depends on the age of the patient. For infants and children up to 12 years the preferred daily dose is between 2 and 10 g and for adults the preferred dose is between 7 and 30 g dietary fibers. Even if the patient is also eating low protein foods, such as fruit and vegetables, it is recommended not to amend the above mentioned daily dose of the fiber composition according to the invention, in order to limit the production of propionic acid by the intestinal microbiota.

A preferred nutritional composition according to the invention comprises between 70 and 250 kcal per 100 ml, and between 1 and 5 g dietary fiber per 100 kcal, more preferably between 1.5 and 4.5 g, even more preferably between 2.0 and 4.0 g dietary fiber per 100 kcal of the nutritional composition. Such a composition was found exceptionally suitable for long term dietary management of MMA and PA patients.

Galacto-oligosaccharides (GOS), also known as oligogalactosyllactose, oligogalactose, oligolactose or transgalactooligosaccharides (TOS), belong to the group of prebiotics. GOS generally comprise a chain of galactose units that arise through consecutive transgalactosylation reactions, with a terminal glucose unit. The degree of polymerization of GOS can vary quite markedly, e.g. ranging from 2 to 8 monomeric units. In a preferred embodiment, the fiber mixture comprises galactooligosaccharides. GOS may be present in the composition up to 100 wt % of the total weight of the fibers, such as 0.5-100 wt %, preferably 1-100 wt % or even 5-100 wt %. Alternatively, further fibers are present and GOS is preferably comprised in the composition in 0.5-90 wt %, preferably 0.5-70 wt %, most preferably 1-30 wt. % based on total weight of the fibers.

Resistant starch (RS) is any starch or starch digestion products that are not digested and absorbed in the stomach or small intestine and pass on to the large intestine. RS has been categorized into four types. Any of these types are suitably used for the present invention. RS1 refers to physically inaccessible or indigestible resistant starch, such as that found in seeds or legumes and unprocessed whole grains. RS2 refers to resistant starch is inaccessible to enzymes due to starch conformation, as in high amylose corn starch. RS3 refers to resistant starch that is formed when starch-containing foods are cooked and cooled, such as pasta. RS3 occurs due to retrogradation, which refers to the collective processes of dissolved starch becoming less soluble after being heated and dissolved in water and then cooled. RS4 refers to starches that have been chemically modified to resist digestion. In a preferred embodiment, the fiber mixture comprises resistant starch. If present, resistant starch is preferably comprised in the composition in 0.5-75 wt. %, preferably 3-50 wt. %, more preferably 10-40 wt. %, most preferably 15-30 wt. % based on total weight of the fibers.

Inulin is a heterogeneous collection of fructose polymers or fructooligosaccharides (FOS). Inulin typically refers to the material as obtained from the plant material, and is commercially available as such. It consists of chain-terminating glucosyl moieties and a repetitive fructosyl moiety, which are linked by $\beta(2,1)$ bonds. The degree of polymerization (DP) of standard inulin ranges from 2 to 60.

After removing the fractions with DP lower than 10 during manufacturing process, the remaining product is termed long chain FOS (lcFOS). The fractions with DP lower than 10 may be referred to as short-chained fructooligosaccharides or scFOS. In a preferred embodiment, the fiber mixture comprises inulin. If present, inulin is preferably comprised in the composition in 0.5-40 wt %, more preferably 5-30 wt %, most preferably 10-25.5 wt %, based on total weight of the fibers.

Next to inulin, it is preferred that oligofructose is present in the fiber mixture according to the invention. Oligofructose are fructooligosaccharides typically having a DP below 10, and is a commercially available product, e.g. as Orafti Oligofructose. In a preferred embodiment, the fiber mixture comprises oligofructose. If present, oligofructose is preferably comprised in the composition in 0.5-50 wt %, preferably 5-50 wt %, most preferably 5-28.4 wt %, based on total weight of the fibers.

Pectins, also known as pectic polysaccharides, are rich in galacturonic acid. Several distinct polysaccharides have been identified and characterised within the pectic group.

Homogalacturonans are linear chains of $\alpha$-(1-4)-linked D-galacturonic acid. In nature, around 80 percent of carboxyl groups of galacturonic acid are esterified with methanol. This proportion is decreased to a varying degree during pectin extraction. The ratio of esterified to non-esterified galacturonic acid determines the behavior of pectin in food applications. This is why pectins are classified as high-vs. low-ester pectins (HM vs. LM-pectins), with more or less than half of all the galacturonic acid esterified. Pectins can be hydrolyzed in order to decrease the molecular weight. For the present application hydrolyzed pectins are preferred in order to prevent undesired increase in viscosity. In a preferred embodiment, the fiber mixture comprises pectin. If present, pectin is preferably comprised in the composition in 0.1-45 wt %, preferably 0.2-27 wt %, preferably 0.5-25 wt %, based on total weight of the fibers.

Cellulose is an organic compound with the formula $(C_6H_{10}O_5)_n$, a polysaccharide consisting of a linear chain of several hundred to many thousands of $\beta(1\rightarrow4)$ linked D-glucose units. Cellulose is not digested or fermented in the human intestine and is therefore a fiber that is excreted in the feces and as such contributes to the consistency of the feces. fiber mixture may comprise cellulose. In a preferred embodiment the fiber mixture comprises less than 5 wt. % cellulose related to dietary fiber in the composition, preferably comprises no cellulose. If present, cellulose may be present in the composition in 0.5-5 wt %, preferably 1-3 wt %, based on total weight of the fibers. Alternatively, cellulose may be present in 0.5-50 wt %, preferably 6-19.6 wt %, based on total weight of the fibers.

Gum Arabic, also known as acacia gum, is a natural gum consisting of the hardened sap of various species of the acacia tree. Arabinogalactan is a biopolymer consisting of arabinose and galactose monosaccharides. It is a major component of many plant gums, including Gum Arabic. In a preferred embodiment, the fiber mixture comprises Gum Arabic. If present, Gum Arabic is preferably comprised in the composition in 0.1-40 wt %, preferably 1-15 wt %, based on total weight of the fibers.

Locust bean gum is a galactomannan vegetable gum extracted from the seeds of the carob tree. It can be used in hydrolyzed or unhydrolyzed form. In a preferred embodiment, the fiber mixture comprises locust bean gum. If present, locust bean gum is preferably comprised in the composition in 0.1-10 wt %, preferably 0.5-3 wt %, based on total weight of the fibers.

Soy polysaccharides, also known as soy fiber, typically refers to the non-starch, largely insoluble polysaccharides isolated from soy bean. When referring to soy polysaccharides in the present invention, they typically have a DP above 10, preferably above 20, more preferably above 50, even more preferably above 100. A suitable source for soy fiber is Fibrim (Solae). In a preferred embodiment, the fiber mixture comprises soy polysaccharides. If present, soy polysaccharides is preferably comprised in the composition in 0.01-10 wt %, preferably 0.05-0.5 wt %, based on total weight of the fibers.

Guar gum is a galactomannan vegetable gum extracted from the seeds of the guar beans. It can be used in (partly) hydrolyzed or unhydrolyzed form. The use of partly hydrolyzed guar gum is most preferred in the context of the present invention. In a preferred embodiment, the fiber mixture comprises partly hydrolyzed guar gum. In an alternative embodiment, the fiber mixture does not contain partly hydrolyzed guar gum as sole dietary fiber. If present, guar gum is preferably comprised in the composition in 0.01-10 wt %, preferably 0.05-3 wt %, based on total weight of the fibers.

Lactic Acid Producing Bacteria

The composition preferably further comprises lactic acid producing bacteria. Alternatively, the dietary fiber composition is administered together with a composition comprising lactic acid producing bacteria. The inventors believe that use of supplemental lactic acid producing bacteria, can synergistically restore and balance intestinal flora microbiota in MMA and PA patients, especially if the presence propionic acid producing bacteria is avoided, thus providing a synergistic effect with the dietary fibers. Hence, in one embodiment, the composition is substantially free from propionic acid producing bacteria. The lactic acid producing bacteria comprised in the composition according to the invention preferably are provided in a daily dose of between $10^8$ Colony Forming Units and $10^{12}$ Colony Forming Units. Preferably the lactic acid producing bacteria are selected from the group that are low propionic acid producing bacteria. Preferably, the composition according to the invention comprises Bifidobacteria and/or Lactobacilli. Preferred strains to be included in the composition according to the invention include *Latobacillus plantarum* (preferably WCFS1) and/or *Bifidobacterium adolescentis* (preferably DSM 18350).

Protein

The composition according to the invention preferably further contains a protein fraction. Preferably, the composition is devoid of intact and partly hydrolyzed protein and the protein fraction consist essentially of free amino acids and dipeptides. Hence, the protein levels defined herein below preferably apply to amino acids only. The term 'protein equivalent' is well understood in the art and refers to the amounts of the free amino acids as if they were part of a protein, i.e. the weight value of amino acids is understood as the protein equivalent weight value. Typically, the contribution of the amino acids to protein represents about 81% of the weight of the individual amino acids.

Amino acids are required for the maintenance of the body cell mass and for virtually all major bodily functions. Protein in the diet serves as a source of essential amino acids and provides nitrogen for the synthesis of other amino acids and nitrogen-containing compounds of physiological importance. Organic Acidurias is caused by the body's inability to breakdown certain precursor amino acids (valine, isoleucine, methionine and threonine) in proteins. Therefore, these amino acids are preferably limited or even completely excluded in the composition according to the invention. In other words, in a preferred embodiment, the protein fraction is substantially devoid of at least two, more preferably at least three, most preferably at least four of valine, isoleucine, methionine and threonine. The table below shows an overview of preferred amino acid profiles according to the invention, in grams per 10 gram protein equivalent.

|  | preferred | more preferred | example |
|---|---|---|---|
| L- Alanine | 0.5-2.2 | 1.0-2.0 | 1.03 |
| L-Arginine | 0.4-1.8 | 0.5-1.5 | 0.90 |
| L-Aspartic Acid | 0.3-1.8 | 0.5-1.5 | 0.82 |
| L-Cystine | 0.2-1.0 | 0.25-0.75 | 0.46 |
| Glycine | 0.2-1.0 | 0.25-0.75 | 0.41 |
| L-Glutamine | 0.5-2.2 | 1.0-2.0 | 1.08 |
| L-Histidine | 0.3-1.8 | 0.5-1.5 | 0.61 |
| L-Isoleucine | 0.0-0.1 | 0.0-0.05 | 0.0 |
| L-Leucine | 0.8-2.5 | 1.0-2.0 | 1.36 |
| L-Lysine | 0.4-2.2 | 0.7-2.0 | 0.91 |
| L-Methionine | 0.0-0.1 | 0.0-0.05 | 0.0 |
| L-Phenylalanine | 0.3-1.8 | 0.5-1.5 | 0.60 |
| L-Proline | 0.2-1.0 | 0.25-0.75 | 0.41 |
| L-Serine | 0.3-1.8 | 0.5-1.5 | 0.59 |
| L-Threonine | 0.0-0.1 | 0.0-0.05 | 0.0 |
| L-Tryptophan | 0.05-0.8 | 0.1 -0.5 | 0.21 |
| L-Tyrosine | 0.3-1.8 | 0.5-1.5 | 0.60 |
| L-Valine | 0.0-0.1 | 0.0-0.05 | 0.0 |

-continued

|  | preferred | more preferred | example |
|---|---|---|---|
| L-Carnitine | 0.0-0.8 | 0.005-0.5 | 0.01 |
| Taurine | 0.0-0.8 | 0.005-0.5 | 0.02 |

The preferred content of the amino acids in the table above applies to each amino acid individually as well as to the entire amino acid profile. Notably, each individual amino acid weight contributes for about 80% to the total protein equivalent weight.

Preferably, the composition according to the invention comprises between 0 and 50 wt % protein equivalent based on the dry weight of the composition, even more preferably between 0 and 40 wt % and most preferably between 20 and 35 wt % based on the dry weight of the composition. In case the composition according to the invention is a nutritional composition, it may preferably comprise between 10 and 60 wt %, preferably between 20 and 50 wt %, more preferably between 25 and 35 wt %, and most preferably about 28 wt % protein equivalent, preferably amino acids, based on dry weight. Per energy unit, the composition according to the invention preferably contains between 2.5 and 10 g amino acids per 100 kcal, preferably between 4 and 9.5 g amino acids per 100 kcal, most preferably between 5 and 8.0 g amino acids per 100 kcal of the composition. Preferably, the composition according to the invention comprises less than 1.0 wt % of each amino acid selected from the group consisting of isoleucine, valine, threonine, and methionine, more preferably less than 0.5 wt %, even more preferably less than 0.1 wt % and most preferably between 0.0 and 0.05 wt % based on total weight of the amino acids in the composition. In a preferred embodiment, the composition according to the invention further comprises carnitine, preferably at least 0.01 wt % carnitine, more preferably between 0.05-7.5 wt %, more preferably between 0.05 and 5 wt % carnitine based on total weight of the amino acids in the composition.

The optimal protein content provided to the patient typically depends on the amount of the composition that is prescribed by the physician or dietitian, according to individual patients' calculated requirements. Protein requirements on average may vary from 1-3 g/kg body weight per day, depending on age and clinical condition. In one embodiment, the composition according to the invention contains sufficient protein to provide 60-100 wt % of the recommended daily intake as set out by the Medical Research Council (MRC) in Recommendations on the dietary management of phenylketonuria. Report of Medical Research Council Working Party on Phenylketonuria. Arch Dis Child, 1993 March 63(3): p. 426-427. In an alternative embodiment, the composition according to the invention contains sufficient protein to provide up to 60 wt % of the recommended daily intake as set out by the MRC, which is particularly preferred in case the composition according to the invention is in the form of a supplement.

Lipids

The composition according to the invention preferably further contains a lipid fraction. Lipid is an important source of energy for children and enables utilization of the amino acids. Certain fatty acids such as long chain polyunsaturated fatty acids (LCPUFAs) are considered beneficial to those on a protein restricted diet. The intake of LCPUFAs in children with inborn errors of amino acid metabolism is typically restricted, as LCPUFA's are predominantly found in foods of animal origin and the dietary therapy requires that such naturally rich sources of protein are excluded from the diet. Lipid also stores lipid soluble vitamins and is a source of essential fatty acids. The overall lipid content of a preferred embodiment is preferable between 2.5 and 9 g lipid per 100 kcal, more preferably between 3 and 7.5 g lipid per 100 kcal, even more preferably between 3.5 and 6 g lipid and most preferably about 4.5 g lipid per q100 kcal or about 12.5-25 g lipid per 100 g dry weight of the composition. Preferably, the source of lipid is a blend of vegetable oils (e.g. a canola-sunflower-palm kernel-coconut oil blend), which provide percentages of saturated (16.6 wt % of fat), polyunsaturated (15.0 wt % of fat) and monounsaturated fatty acids (68.4 wt % of fat). Preferably the nutritional composition according to the invention comprises the essential fatty acids, linoleic acid (C18:2 (n–6)) and alpha-linolenic acid (C18:3 (n–3)) and are preferably present in amounts which are in line with current recommendations (3 to 10 wt % and 0.5 to 4.5 wt % of total lipid weight). The ratio of n–6 to n–3 fatty acids is preferably in the range 6:1-1:1, more preferably 3:1-2:1, most preferably about 2.6:1. Docosahexaenoic Acid (22:6n–3, DHA) is an important omega-3 long chain polyunsaturated (LCP) fatty acid, as it is the most prominent fatty acid in neural tissue. It accounts for approximately 20% of all fatty acids in the brain and up to 60% of all fatty acids in the retina (eyes). DHA is essential for formation of neural membranes, membrane integrity, electrical insulation, vesicular trafficking and synaptic transmission. Research has shown that the conversion of DHA from its precursor essential fatty acid ALA is less efficient than was generally assumed. As DHA has been found to be lacking in the diet and plasma of PKU subjects following restricted diets and also in those with other inborn errors of metabolism DHA has been included in the compositions according to the invention at a level of between 20-120 mg, preferably between 30 and 90 mg, even more preferably between 35 and 85 mg, most preferably about 65 mg per 100 kcal. The source of DHA is preferably a marine algae which has minimal effect on the taste of the finished product compared to sources from fish oil.

Digestible Carbohydrate

The composition according to the invention preferably further contains a digestible carbohydrate fraction. Carbohydrates are classified into monosaccharides, disaccharides, oligosaccharides, and polysaccharides. Digestible carbohydrate include important biomolecules that are an important source of energy. Preferably, the overall carbohydrate content of is the composition according to the invention is between 0 and 50 g, preferably between 20 and 40 g, most preferably about 30 g per 100 kcal. Preferably, the source of carbohydrate in the composition according to the invention comprises, preferably is, maltodextrin. The use of maltodextrin enhances solubility and reduces contribution to the osmolality of the formula compared to e.g. glucose or saccharose.

Micronutrients

The composition according to the invention preferably further contains micronutrients. Preferably, the composition according to the invention comprises vitamins, minerals and trace elements in amounts to meet the RDA/DRI and DRV for a 1-3 year old based on typical product usage (see e.g. Institute of Medicine, Dietary Reference Intakes for Calcium and Vitamin D, National Academy Press, Editor 2010: Washington D.C.). In particular vitamin D and calcium have been increased in line with new recommended intakes as discussed below. Sodium and potassium have been deliberately reduced in order to optimize taste.

In a preferred embodiment, the composition according to the invention comprises vitamin D and/or calcium, preferably vitamin D.

The major source of vitamin D for humans is exposure to sunlight, and anything that prevents sun exposure or interferes with the penetration of UVB into the skin will affect the synthesis of vitamin D. There are a few dietary sources providing vitamin D. The major sources are fatty fish, fish oils, liver and other organ meats, and egg yolks of chickens fed vitamin D, which are generally excluded from the restricted diets of patients with inborn errors of metabolism. Vitamin D deficiency in children will cause growth retardation and classic signs and symptoms of rickets. Vitamin D is critical to bone health, and as the foundations of adult bone health are laid down in early years, adequate intake of vitamin D during childhood is fundamental. Suboptimal vitamin D status and/or suboptimal exposure to sunlight is also associated with muscle weakness, functional deficits, cardiovascular disease, cancer mortality and perhaps longer length of stay of hospitalized patients. Furthermore, vitamin D has a pivotal role supporting serum calcium concentrations within narrow limits, and is crucial for maximizing absorption of calcium in the small intestine. It has been estimated that adequate vitamin D status increases calcium absorption to 30-40% compared to 10-15% when vitamin D status is insufficient. Factors affecting vitamin D status include race, poor nutrition, advanced age, use of multivitamins, and ultraviolet light exposure. Patients with inborn errors of metabolism are expected to have very limited intake of vitamin D from their normal diet. Therefore, the composition according to the invention preferably comprises between 2-20 µg, more preferably between 4 and 17 µg, most preferably between 5 and 14 µg/100 kcal (200-560 IU/100 kcal) of vitamin D.

Calcium is an essential nutrient used in the mineralization of bones and teeth. Furthermore, calcium is used as a signal for many cellular processes, e.g. secretion of hormones, enzymes and the nervous system. Calcium and vitamin D are closely linked to each other. The major physiologic function of vitamin D is to maintain serum calcium and phosphorus levels within normal ranges to support e.g. metabolic functions, bone mineralization. In case of inadequate calcium intake, vitamin D helps to maintain calcium homeostasis. However, when vitamin D is deficient, it prevents efficient absorption of calcium. Preferably, the composition according to the invention comprises calcium at a level of between 200 and 600 mg, more preferable between 250 and 500 mg, and most preferably about 375 mg per 100 kcal. Per 100 g dry weight of the composition, the calcium content is preferably 500-1500 mg, more preferably 800-1200 mg, most preferably about 980 mg.

Caloric Density

In a preferred embodiment, the composition according to the invention is a supplement containing only dietary fibers. The fiber thus constitutes about 90-100 en % of the composition. In another preferred embodiment, the composition according to the invention is a supplement containing only dietary fiber and protein. In the latter embodiment, the caloric density of protein is preferably between 4 and 98 en % and the caloric density of dietary fiber is preferably between 2 and 96 en %. In another preferred embodiment, the composition according to the invention is a complete nutritional composition comprising dietary fiber, protein, digestible carbohydrates and lipids, wherein the caloric density is preferably as follows: 10-60 en % lipids, 10-65 en % digestible carbohydrates, 2.0-15 en % dietary fibers, and 10-40 en % protein. The caloric density of the complete nutritional composition is preferably 0.4-3.5 kcal/ml, more preferably 0.7-3.0 kcal, even more preferably 0.8-2.6 kcal and most preferably 0.9-2.4 kcal/ml. Herein, "containing only" means that other components are substantially absent, and all caloric densities of the components are given as percentage of total caloric content of the composition.

Especially Preferred Compositions

In one aspect of the invention, the invention concerns the composition itself as defined above. In the context of this aspect, the composition according to the invention preferably comprises dietary fibers and a protein fraction consisting of free amino acids. An especially preferred composition according to the invention comprises galactooligosaccharides, resistant starch, Gum arabic, soy polysaccharides and at least one of oligofructose and inulin, preferably combined with a protein fraction consisting of free amino acids, more preferably wherein the free amino acids substantially devoid of valine, isoleucine, methionine and threonine. A further preferred composition comprises at least one dietary fiber selected from the group consisting of oligofructose, inulin, resistant starch, cellulose, methylcellulose, wheat bran, gum arabic, soy polysaccharides, oat fiber, galactooligosaccharides, locus bean gum, pectin, guar gum and mixtures thereof, and free amino acids substantially devoid of valine, isoleucine, methionine and threonine. Preferably, the dietary fibers comprise at least GOS. Preferably, the composition further comprises lactic acid bacteria. It is especially preferred that the composition according to the present aspect further comprises 10-60 en % lipids and 10-65 en % digestible carbohydrates and wherein the dietary fibers are present in 2.0-25 en % and the protein is present in 10-40 en % of total composition and wherein the caloric density of the composition is 0.7-3.5 kcal/ml.

Application

In a first aspect, the composition according to the present invention, comprising dietary fibers, is for use in the dietary management of methylmalonic acidemia (MMA) and/or propionic acidemia (PA). In other words, the invention concerns the use of dietary fibers for the manufacture of a composition for use in the dietary management of methylmalonic acidemia (MMA) and/or propionic acidemia (PA). In other words, the invention concerns a method for dietary managing methylmalonic acidemia (MMA) and/or propionic acidemia (PA), comprising administering to a subject in need thereof the composition according to the invention, comprising a therapeutic amount of dietary fibers.

Further, the composition according to the present invention, comprising dietary fibers, is for use in treating and/or reducing methylmalonic acidemia (MMA) and/or propionic acidemia (PA), and/or treating, reducing and/or preventing symptoms associated therewith. In other words, the invention concerns the use of dietary fibers for the manufacture of a composition for use in treating and/or reducing methylmalonic acidemia (MMA) and/or propionic acidemia (PA), and/or treating, reducing and/or preventing symptoms associated therewith. In other words, the invention concerns a method for treating and/or reducing methylmalonic acidemia (MMA) and/or propionic acidemia (PA), and/or treating, reducing and/or preventing symptoms associated therewith, comprising administering to a subject in need thereof the composition according to the invention, comprising a therapeutic amount of dietary fibers.

Further, the composition according to the present invention, comprising dietary fibers, is for use in reducing gut flora induced production of propionic acid. In other words, the invention concerns the use of dietary fibers for the manufacture of a composition for use in reducing gut flora induced production of propionic acid. In other words, the invention concerns a method for reducing gut flora induced production of propionic acid, comprising administering to a subject in need thereof the composition according to the invention, comprising a therapeutic amount of dietary fibers.

Whatever said here regarding the use(s) according to the invention equally applies to the method(s) according to the invention and the composition(s) for use according to the invention. These uses are medical in nature. The target group for these uses are patients suffering from MMA and/or PA. The uses according to the invention typically involve decreasing the production of propionic acid by the gut flora as measured in the feces of the patient.

The use according to the first aspect may further be for treating and/or reducing MMA or PA, and/or treating, reducing and/or preventing symptoms associated therewith. In one embodiment, the use according to the first aspect is further for treating and/or reducing MMA and/or PA. In one embodiment, the use according to the first aspect is further for treating, reducing and/or preventing symptoms associated with MMA and/or PA.

In one embodiment, the use according to the second aspect is for treating and/or reducing MMA and/or PA. In one embodiment, the use according to the second aspect is for treating, reducing and/or preventing symptoms associated with MMA and/or PA. The use according to the second aspect may further be for the dietary management of MMA and/or PA. Treating, reducing and/or preventing symptoms may also be referred to as alleviating symptoms.

Symptoms associated with MMA and/or PA may also be referred to as symptoms associated with overproduction of propionic acid in the intestine, and typically include intestinal disorders, disorders associated with a vitamin D deficiency and disorders associated with a LC-PUFA deficiency. The intestinal disorders in MMA and/or PA patients typically include one or more of imbalanced microbiota, bacterial translocation, impaired stool bulking properties, impaired gut transit time, imbalanced SCFA production and constipation. In one embodiment, the intestinal disorder is selected from impaired stool bulking properties, imbalanced SCFA production and constipation. Stool bulking products include bulk, consistency and viscosity. Reducing imbalances SCFA production preferably includes balancing the SCFA production along the length of the colon. The disorders associated with a vitamin D deficiency in MMA and/or PA patients typically include one or more of growth retardation, rickets, impaired bone health, muscle weakness, functional deficits, cardiovascular disease, cancer mortality and impaired calcium uptake. The disorders associated with a LC-PUFA deficiency, in particular DHA-deficiency, include brain disorders such as impaired neural membrane integrity, impaired electrical insulation, impaired vesicular trafficking and impaired synaptic transmission. These symptoms associated with MMA and/or PA are treated, reduced and/or prevented by administration of the composition according to the invention. In a preferred embodiment, the intestinal disorders associated with MMA and/or PA are treated, reduced and/or prevented.

Example 1

Fermentations

The effects of the fiber mixtures of table 1 on SCFA production were measured after 24 hour incubation in a high-throughput anaerobic colon model (I-Screen™ platform, TNO, Zeist, the Netherlands). This platform simulates the gut microbiota conditions and allows for determining effects of the compounds on the composition of the microbiota over time under strictly anaerobic conditions. The I-Screen™ model was inoculated with a standardized healthy human adult gut microbiota. The gut microbiota was obtained by pooling fecal samples from 6 healthy adult volunteers and incubating the pooled fecal samples in a fed-batch fermenter for 40 h to create a standardized microbiota. The pooled fecal samples were then cultured in vitro in modified standard ileal efflux medium (SIEM) and the pH was adjusted to 5.8. This standard adult gut microbiota was stored at $-80°$ C. in 12% glycerol until further analyses. This pooling approach aims to limit inter-individual variations and increase the probability to have a larger representation of potential bacterial species in the human colon.

Before testing the fiber mixtures, the standard adult microbiota was activated by incubating it overnight in the modified SIEM medium under anaerobic conditions, at $37°$ C. and with shaking at 300 rpm. 4 conditions, corresponding to different combinations of fiber mixtures and components (table 1), were tested in the concentration of 6 mg/ml (concentration at fiber level). A negative control (unexposed microbiota with SIEM medium) and a blank (SIEM medium without microbiota) were included. Each condition, including the controls, was tested in triplicate. Table 1 summarizes the experimental setup. After adding the (combinations of) test compounds, the negative control or the blank, the microbiota was incubated anaerobically for 24 h at $37°$ C. Samples were then collected and processed for further analyses.

Short Chain Fatty Acid (SCFA) Measurement

For the analysis of short chain fatty acids, material resulting from the I-Screen™ incubation was sampled and centrifuged at 4,000 g for 5 minutes. The supernatant was filter sterilized using 0.45 pm filters. A mixture of formic acid (20%), methanol and 2-ethyl butyric acid (internal standard, 2 mg/ml in methanol) was added. A 3 pl sample with a split ratio of 75.0 was injected on a GC-column (ZB-5HT inferno, ID 0.52 mm, film thickness 0.10 um; Zebron; phenomenex, USA) in a Shimadzu GC-2014 gas chromatograph. The SCFA analyzed were acetic acid, propionic acid, iso-butyric acid, n-butyric acid and iso-valeric acid.

Results

The amount of propionic acid produced and the percentage propionic acid relative to total SCFA for the fibers mixtures after the 24 hour, anaerobic, in vitro fermentations with adult microbiome is shown in table 2. Mixes A, B, D, E and F reduce the formation of propionic acid compared to the control, and increase the total amount of SCFA formed, whereas mix C gives rise to increased propionic acid formation. Moreover, Mix B (GOS) shows the greatest effect both in terms of propionic acid and SCFA formation. over mix A and C. Next to this mix D, for which compared to mix A the level of resistant starch is increased (at the cost of cellulose), demonstrates a decrease in propionic acid over mix A. Also the total amount of SCFA is higher for mix D compared to mix A. Adding 10 wt. % GOS to mix D further lowers the amount of propionic acid in resultant mix F. The effect on proprionic acid of GOS seems higher when a relative high amount of resistant starch is present. Mix F versus mix D demonstrates an improved effect compared to mix E versus mix A.

Conclusion

The inventors have found that the fiber mixtures according to the invention result in lower levels of propionic acid production in the adult microbiome. In particular mix B, D and F are surprisingly low in propionic acid production, while maintaining high production of the other SCFA. This indicates that the fiber compositions comprising fibers according to the invention could play an important role in clinical features of patients with methylmalonic acidemia (MMA) and propionic acidemia (PA).

TABLE 1

Composition of the tested fiber mixes (in weight percentage of each fiber relative to total fiber).

|  | Mix A | Mix B | Mix C | Mix D | Mix E | Mix F |
|---|---|---|---|---|---|---|
| Oligofructose | 28.4 | 0 | 0 | 28.4 | 25.6 | 25.6 |
| Resistant starch | 8.6 | 0 | 0 | 25.0 | 7.7 | 22.5 |
| Inulin | 25.5 | 0 | 0 | 25.5 | 23.0 | 23.0 |
| Gum arabic | 15.0 | 0 | 0 | 15.0 | 13.5 | 13.5 |
| Cellulose | 19.6 | 0 | 0 | 3.1 | 17.6 | 2.8 |
| Soy PS | 0.4 | 0 | 0 | 0.4 | 0.4 | 0.4 |
| Guar Gum | 2.4 | 0 | 0 | 2.4 | 2.4 | 2.4 |
| Galactooligosaccharides (GOS) | 0 | 100.0 | 0 | 0 | 10.00 | 10.0 |
| Locust bean gum (LBG) | 0 | 0 | 100 | 0 | 0 | 0 |

TABLE 2

Propionic acid produced upon in-vitro fermentation (average of 3 measurements).

| Fiber mix | Propionic acid (mMol/L) | Relative change (%) | Total SCFA (mMol/L) | Propionic acid (% of total SCFA) |
|---|---|---|---|---|
| Control | 11.8 |  | 64.7 | 18.2 |
| Mix A | 10.5 | −11.0 | 80.8 | 13.0 |
| Mix B | 9.2 | −22.0 | 97.4 | 9.5 |
| Mix C | 21.2 | 79.7 | 80.1 | 26.4 |
| Mix D | 9.0 | −23.7 | 85.6 | 10.2 |
| Mix E | 10.3 | −12.7 | 85.0 | 12.1 |
| Mix F | 8.5 | −28.0 | 85.6 | 10.0 |

Example 2: Composition According to the Invention

The follow composition according to the invention is a composition suitable for treating MMA and PA by modulation of intestinal microbiota resulting in low propionic acid production. The supplement comprises, in wt % based on total weight of the composition:
1.5-28.4% oligofructose
1.5-25.5% inulin
1.5-50% resistant starch
1-15% gum arabic
0-0.5% soy polysaccharides
0-3% guar gum
5-79.5% galactooligosaccharide
Optionally supplemented with lactic acid producing bacteria, preferably Bifidobacteria and/or Lactobacilli.

Example 3: Composition According to the Invention

The follow composition according to the invention is a composition suitable for treating MMA and PA by modulation of intestinal microbiota resulting in low propionic acid production. The supplement comprises, in wt % based on total weight of the supplement:
5-100% galactooligosaccharides
0-70% resistant starch
Optionally supplemented with lactic acid producing bacteria, preferably Bifidobacteria and/or Lactobacilli.
Optionally a lipid source and digestible carbohydrate source Example 4: Composition According to the Invention The follow composition according to the invention is a composition for the treatment and or dietary management of MMA or PA patients by modulating the intestinal microbiota and supplementing protein resulting a low toxic metabolites levels in blood. The composition comprises the fiber blend according to example 2 and an amino acid blend comprising, in grams per 10 gram protein equivalent:

| L-Alanine | 1.23 |
|---|---|
| L-Arginine | 1.08 |
| L-Aspartic Acid | 0.98 |
| L-Cystine | 0.56 |
| Glycine | 0.49 |
| L-Glutamine | 1.30 |
| L-Histidine | 0.73 |
| L-Isoleucine | 0.0 |
| L-Leucine | 1.63 |
| L-Lysine | 1.10 |
| L-Methionine | 0.0 |
| L-Phenylalanine | 0.72 |
| L-Proline | 0.49 |
| L-Serine | 0.71 |
| L-Threonine | 0.0 |
| L-Tryptophan | 0.25 |
| L-Tyrosine | 0.72 |
| L-Valine | 0.0 |
| L-Carnitine | 0.01 |
| Taurine | 0.02 |

Example 5: Composition According to the Invention

The follow composition according to the invention is a complete nutritional composition for the treatment and/or dietary management of MMA or PA patients by modulating the intestinal microbiota and supplementing protein resulting a low toxic metabolites levels in blood. This composition can be used as exclusive diet. The supplement comprises the fiber and protein blend according to example 3, lipids, digestible carbohydrate and micronutrients.

| Component | Unit | invention formula (per 100 g dry weight) |
|---|---|---|
| Energy | kcal | 367 |
| Protein equivalents * | g | 28 |
| Carbohydrates | g | 30 |
| Fat | g | 12.5 |
| DHA (22:6n–3) | mg | 180 |
| Micronutrients | | |
| Na | mg | 385 |
| K | mg | 613 |
| Cl | mg | 560 |
| Ca | mg | 1348 |
| P | mg | 885 |
| Mg | mg | 154 |
| Fe | mg | 13.6 |
| Zn | mg | 6.6 |
| Cu | µg | 780 |
| Mn | mg | 1.3 |
| F | mg | — |
| Mo | µg | 35.0 |
| Se | µg | 38.5 |
| Cr | µg | 14.0 |
| I | µg | 174 |
| Vit A | µg RE | 525 |
| Vit D | µg | 26.3 |
| Vit E | mg-α-TE | 10.5 |
| Vit K | µg | 17.5 |
| Thiamin (B1) (as base) | mg | 0.91 |
| (as HCl) | mg | — |
| Riboflavin (B2) | mg | 0.91 |
| Niacin (B3) | mg NE | 14.0 |
| Niacin (B3) | mg | — |
| Pant. Acid (B5) | mg | 5.3 |
| Vit B6 | mg | 0.91 |
| Folic acid (B9) | µg | 263 |
| Vit B12 | µg | 1.6 |
| Biotin (B8) | µg | 14.0 |
| Vit C | mg | 52.5 |
| Choline | mg | 280 |
| Myo-inositol | mg | 70.0 |
| Amino Acids | | |
| L- Alanine | g | 3.42 |
| L-Arginine | g | 3.00 |
| L-Aspartic Acid | g | 2.72 |
| L-Cystine | g | 1.56 |
| Glycine | g | 1.37 |
| L-Glutamine | g | 3.61 |
| L-Histidine | g | 2.02 |
| L-Isoleucine | g | <0.025 |
| L-Leucine | g | 4.54 |
| L-Lysine | g | 3.05 |
| L-Methionine | g | 0.00 |
| L-Phenylalanine | g | 1.99 |
| L-Proline | g | 1.37 |
| L-Serine | g | 1.98 |
| L-Threonine | g | 0.00 |
| L-Tryptophan | g | 0.69 |
| L-Tyrosine | g | 1.99 |
| L-Valine | g | 0.00 |
| L-Carnitine | g | 0.02 |
| Taurine | g | 0.06 |
| Probiotics | CFU | $10^8$-$10^{12}$ |
| Bifidobacterium adolescentis (DSM 18350) | | |
| Fiber | g | 4.2-11.2 |
| oligofructose | wt %/total fiber | 2.5-28.4 |
| inulin | wt %/total fiber | 2.5-25.5 |
| resistant starch | wt %/total fiber | 3-50 |
| gum arabic | wt %/total fiber | 1-15 |
| soy polysaccharides | wt %/total fiber | 0-0.5 |
| guar gum | wt %/total fiber | 0-3 |
| GOS | wt %/total fiber | 5-79.5 |

Note
* The term 'protein equivalent' is well understood in the art and refers to the amounts of the free amino acids as if they were part of a protein, i.e. the weight value of amino acids is understood as the protein equivalent weight value. The contribution of the amino acids to protein represents about 81% of the weight of the individual amino acids.

The invention claimed is:

1. A method for:
   treating and/or reducing methylmalonic acidemia (MMA) and/or propionic acidemia (PA);
   dietary management of MMA and/or PA; and/or
   reducing gut flora induced production of propionic acid,
   in a human subject having an age of at least 3 years and suffering from MMA or PA, wherein the method comprises administering to the human subject a composition comprising a fiber mixture, wherein the fiber mixture comprises galactooligosaccharides and 1.5-25 wt % resistant starch based on a total weight of the fiber mixture.

2. The method according to claim 1, wherein the subject has an age of at least 12 years.

3. The method according to claim 1, wherein the composition further comprises Gum arabic, soy polysaccharides and at least one of oligofructose and inulin.

4. A method for:
   treating and/or reducing methylmalonic acidemia (MMA) and/or propionic acidemia (PA);
   dietary management of MMA and/or PA; and/or
   reducing gut flora induced production of propionic acid,
   in a patient suffering from MMA or PA, wherein the method comprises administering to the patient a composition comprising a fiber mixture, wherein the fiber mixture comprises galactooligosaccharides, 1.5-25 wt % resistant starch based on a total weight of the fiber mixture, Gum Arabic, soy polysaccharides and at least one of oligofructose and inulin.

5. The method according to claim 1, wherein the composition comprises at least 10 wt. % resistant starch, based on the total weight of the fiber mixture.

6. The method according to claim 1, wherein the composition comprises at least 20 wt. % of the combination of resistant starch and galactooligosaccharides, based on the total weight of the fiber mixture.

7. The method according to claim 1, wherein the composition further comprises lactic acid producing bacteria.

8. The method according to claim 4, wherein the composition further comprises guar gum.

9. The method according to claim 4, wherein the composition comprises less than 5 wt. % cellulose, based on the total dietary fiber weight of the fiber mixture.

10. The method according to claim 1, wherein the composition is in the form of: (i) a nutritional supplement, wherein the supplement comprises amino acids; or (ii) a complete nutritional composition, wherein the nutritional composition comprises a protein fraction, optionally in the form of amino acids, digestible carbohydrates, vitamins and minerals.

11. The method according to claim 1, wherein the composition further comprises a protein fraction consisting essentially of free amino acids and dipeptides.

12. The method according to claim 1, wherein the composition comprises DHA.

13. The method according to claim 1, wherein the composition comprises vitamin D and/or calcium.

14. A method for:
treating and/or reducing methylmalonic acidemia (MMA) and/or propionic acidemia (PA);
dietary management of MMA and/or PA; and/or
reducing gut flora induced production of propionic acid,
in a human subject having an age of at least 3 years and suffering from MMA or PA, wherein the method comprises administering to the human subject a composition comprising a fiber mixture, wherein the fiber mixture comprises 1.5-28.4 wt % oligofructose, 1.5-25.5 wt. % inulin, 1.5-25 wt. % resistant starch, 1-15 wt. % Gum arabic, 0-0.5 wt. % soy polysaccharides, 0-3 wt. % guar gum and 5-79.5 wt. % galactooligosaccharides, based on a total weight of the fiber mixture.

* * * * *